United States Patent
Li et al.

(10) Patent No.: US 12,180,210 B2
(45) Date of Patent: Dec. 31, 2024

(54) COMPOUNDS

(71) Applicant: INTRA-CELLULAR THERAPIES, INC., New York, NY (US)

(72) Inventors: Peng Li, New Milford, NJ (US); Hailin Zheng, New York, NY (US)

(73) Assignee: INTRA-CELLULAR THERAPIES, INC., Bedminster, NJ (US)

(*) Notice: Subject to any disclaimer, the term of this patent is extended or adjusted under 35 U.S.C. 154(b) by 910 days.

(21) Appl. No.: 17/288,225

(22) PCT Filed: Oct. 23, 2019

(86) PCT No.: PCT/US2019/057549
§ 371 (c)(1),
(2) Date: Apr. 23, 2021

(87) PCT Pub. No.: WO2020/086650
PCT Pub. Date: Apr. 30, 2020

(65) Prior Publication Data
US 2022/0064169 A1 Mar. 3, 2022

Related U.S. Application Data

(60) Provisional application No. 62/749,518, filed on Oct. 23, 2018.

(51) Int. Cl.
*C07D 487/04* (2006.01)
*A61P 25/00* (2006.01)

(52) U.S. Cl.
CPC ............ *C07D 487/04* (2013.01); *A61P 25/00* (2018.01)

(58) Field of Classification Search
CPC ................................ C07D 487/04; A61P 25/00
See application file for complete search history.

(56) References Cited

U.S. PATENT DOCUMENTS

| | | | | |
|---|---|---|---|---|
| 9,200,000 B2 * | 12/2015 | Helal | ................ | C07D 487/04 |
| 2014/0066622 A1 | 3/2014 | Helal et al. | | |
| 2014/0349970 A1 * | 11/2014 | Wishart | ................ | C07D 498/14 |
| | | | | 514/250 |

FOREIGN PATENT DOCUMENTS

WO    WO 2016/090380 A1    6/2016

OTHER PUBLICATIONS

Bubb et al., "Inhibition of Phosphodiesterase 2 Augments cGMP and cAMP Signaling to Ameliorate Pulmonary Hypertension," Circulation, pp. 496-507, (2014); DOI: 10.1161/CIRCULATIONAHA. 114.009751.
Domek-Lopacinska et al., "The effect of selective inhibition of cyclic GMP hydrolyzing phosphodiesterases 2 and 5 on learning and memory processes and nitric oxide synthase activity in brain during aging," Brain Res., vol. 1216, pp. 68-77, (2008).
Gomez et al., "PDE2 inhibition: Potential for the treatment of cognitive disorders," Bioorg. Med. Chem. Lett., vol. 23, pp. 6522-6527, (2013).
Masood et al., "Reversal of Oxidative Stress-Induced Anxiety by Inhibition of Phosphodiesterase-2 in Mice," J. Pharmacol. Exp. Ther., vol. 326, No. 2, pp. 369-379, (2008).
Masood et al., "Anxiolytic Effects of Phosphodiesterase-2 Inhibitors Associated with Increased cGMP Signaling," JPET, vol. 331, No. 2, pp. 690-699, (2009).
PubChem, "8-(3,3-Difluoroazetidin-1-yl)-3-methyl-1-[1-methyl-5-(4-methylphenyl)pyrazol-4-yl]imidazo[1,5-a]pyrazine," U.S. National Library of Medicine, (2015), database accession No. 89988495. 20 pages.
PubChem, 8-(Azetidin010y1)-3-methyl-1-(1-methylpyrazol-4-yl)imidazo[1,5-a]pyrazine, U.S. National Library of Medicine, (2015), database accession No. 89988494. 20 pages.
Xu et al., "The effects of curcumin on depressive-like behaviors in mice," Eur. J. Pharmacol., vol. 518, pp. 40-46, (2005); DOI: 10.1016/j.ejphar.2005.06.002.
Xu et al., "Phosphodiesterase-2 inhibitor reverses corticosterone-induced neurotoxicity and related behavioral changes via cGMP/PKG dependent pathway," Intl. J. Neuropsychopharmacol., vol. 16, pp. 835-847, (2013); https://doi.org/10.1017/S146114571200065X.

* cited by examiner

*Primary Examiner* — Jeffrey S Lundgren
*Assistant Examiner* — Alexander K. Showalter
(74) *Attorney, Agent, or Firm* — Hoxie & Associates LLC

(57) ABSTRACT

The present disclosure relates to novel PDE2 inhibitory compounds of Formula I as described herein, their use as pharmaceuticals and pharmaceutical compositions comprising them.

20 Claims, No Drawings

COMPOUNDS

CROSS-REFERENCE TO RELATED APPLICATIONS

This application is a U.S. National Stage application under 35 U.S.C. § 371 of International Application No. PCT/US2019/057549, filed on Oct. 23, 2019, which claims priority to and the benefit of U.S. Provisional Application Ser. No. 62/749,518, filed Oct. 23, 2018, the contents of which are hereby incorporated by reference in its entirety.

TECHNICAL FIELD

The present disclosure relates to PDE2 inhibitory compounds of Formula I as described below, their use as pharmaceuticals and pharmaceutical compositions comprising them. These compounds are useful e.g., in the treatment of PDE2-mediated disorders such as anxiety, depression, autism spectrum disorder (ASD), schizophrenia and cognitive impairment.

BACKGROUND OF THE DISCLOSURE

PDE2 is a 105-KDa homodimer that is expressed in a wide variety of tissues and cell types including brain (including hippocampus, striatum and prefrontal cortex), heart, platelets, endothelial cells, adrenal glomerulosa cells and macrophages. Although cGMP is the preferred substrate and effector molecule for this enzyme, PDE2 hydrolyzes both cyclic adenosine monophosphate (cAMP) and cyclic guanosine monophosphate (cGMP) and is thought to be involved in several physiological processes. Specifically, it has been shown that inhibition of nitric oxide synthase (NOS), which reduces cGMP signaling, attenuates the behavioral effects of the benzodiazepine chlordiazepoxide, an anxiolytic compound. Also, commercially-available tool inhibitors of PDE2 such as Bay 60-7550 has been shown to increase cyclic nucleotide levels in the brain and have significant anti-anxiety and anti-depressant effects in normal and stressed rodents (Xu et al., *Eur. J. Pharmacol.* (2005) 518:40-46; Masood et al., *J. Pharmacol. Exp. Ther.* (2008) 326:369-379; Masood et al., *JPET* (2009) 331:690-699; Xu et al., *Intl. J. Neuropsychopharmacol.* (2013) 16:835-847). Inhibition of PDE2 by Bay 60-7550 have also been shown to elevate cGMP and cAMP levels in stimulated primary neuronal cultures in a dose responsive manner; enhance Long-Term Potentiation (LTP) in hippocampal slice preparations in response to electrical stimulation; enhance learning in novel object recognition animal model and a social recognition task in rats; improve acquisition and consolidation phases of novel object memory in age impaired rats; improve performance on object location and recognition tasks when administered after training. Gomez et al., *Bioorg. Med. Chem. Lett.* (2013) 23:6522-6527. Bay 60-7550 has also been shown to improve cognition and memory function in rats through the enhancement of neuronal NOS activity in the brain. (Domek-Lopacinska et al. (2008) *Brain Res.* 1216:68-77). Therefore, PDE2 plays an important role in effective behaviors and cognitive function.

In addition to effective behavior and cognitive function, it has been observed that in endothelial cells, PDE2A mRNA and activity are highly induced in response to tumor necrosis factor-α stimulation in vitro. Selective inhibition of PDE2 activity with 9-(6-phenyl-2-oxohex-3-yl)-2-(3,4-dimethoxybenzyl)-purin-6-one (PDP) greatly alters the barrier function of endothelial cells, suggesting that PDE2 is likely to play an important role in regulating fluid and protein integrity of the circulatory system under pathological conditions. Therefore, PDE2 may be a good pharmacological target for sepsis or in more localized inflammatory responses.

In a recent study, PDE2 inhibition has also been shown to elicit pulmonary dilation, prevents pulmonary vascular remodeling and reduces the right ventricular hypertrophy characteristic of pulmonary hypertension, suggesting therapeutic potential of PDE2 inhibition in pulmonary hypertension. Bubb et al., "Inhibition of Phosphodiesterase 2 Augments cGMP and cAMP Signaling to Ameliorate Pulmonary Hypertension", Circulation, Aug. 5, 2014, p. 496-507, DOI: 10.1161/CIRCULATIONAHA.114.009751.

Despite the promising preclinical data and the identification of PDE2 as a promising drug target, no PDE2 inhibitors are currently known to be under clinical investigation due in part to the poor metabolic stability and inability to cross blood-brain barrier and thus have poor brain penetrance of existing PDE2 compounds. There is, therefore, a need for compounds that selectively inhibit PDE2 activity while demonstrate superior biophysical and physiochemical properties.

SUMMARY OF THE DISCLOSURE

The disclosure provides novel compounds having potent and selective PDE2 inhibitory properties with improved orally availability and brain access. Therefore, in the first aspect, the disclosure provides a compound of Formula I:

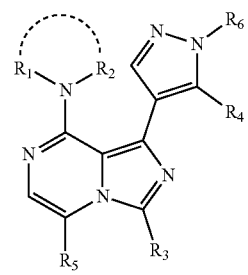

Formula I wherein
(i) $R_1$ and $R_2$ together with the nitrogen atom form a heteroC$_{3-7}$cycloalkyl (e.g., forms an azetidin-1-yl);
(ii) $R_3$ is H or C$_{1-4}$alkyl (e.g., methyl);
(iii) $R_4$ is heteroaryl, halo (e.g., chloro), cyano or aryl (e.g., phenyl) optionally substituted with one or more groups selected from C$_{1-4}$alkyl (e.g., ethyl), C$_{3-7}$cycloalkyl (e.g., cyclopropyl), C$_{1-4}$alkoxy (e.g., methoxy) and haloC$_{1-4}$alkyl (e.g., trifluoromethyl);
(iv) $R_5$ is H or C$_{1-4}$alkyl (e.g., methyl); and
(v) $R_6$ is H or C$_{1-4}$alkyl (e.g., methyl);
in free or salt form.

The disclosure further provides the compound of Formula I as follows:
1.1 Formula I, wherein $R_1$ and $R_2$ together with the nitrogen atom form a heteroC$_{3-6}$cycloalkyl (e.g., azetidin-1-yl).
1.2 Any of the preceding Formulae, wherein $R_1$ and $R_2$ together with the nitrogen atom form an azetidin-1-yl.
1.3 Any of the preceding Formulae, wherein $R_3$ is C$_{1-4}$alkyl (e.g., methyl).
1.4 Any of the preceding Formulae, wherein $R_3$ is methyl.

1.5 Any of the preceding Formulae, wherein $R_4$ is aryl (e.g., phenyl) substituted with one or more groups selected from $C_{1-4}$alkyl (e.g., methyl, ethyl, or propyl, e.g., isopropyl), $C_{3-7}$cycloalkyl (e.g., cyclopropyl), $C_{1-4}$alkoxy (e.g., methoxy) and halo$C_{1-4}$alkyl (e.g., trifluoromethyl).

1.6 Formula I or any of Formulae 1.1-1.5, wherein $R_4$ is aryl (e.g., phenyl) substituted with $C_{1-4}$alkyl (e.g., methyl, ethyl, or propyl, e.g., isopropyl).

1.7 Formula I or any of Formulae 1.1-1.5, wherein $R_4$ is aryl (e.g., phenyl) substituted with $C_{3-7}$cycloalkyl (e.g., cyclopropyl).

1.8 Formula I or any of Formulae 1.1-1.5, wherein $R_4$ is aryl (e.g., phenyl) substituted with $C_{1-4}$alkoxy (e.g., methoxy).

1.9 Formula I or any of Formulae 1.1-1.5, wherein $R_4$ is aryl (e.g., phenyl) substituted with halo$C_{1-4}$alkyl (e.g., trifluoromethyl).

1.10 Any of the preceding Formulae, wherein $R_5$ is H.

1.11 Formula I or any of Formulae 1.1-1.9, wherein $R_5$ is $C_{1-4}$alkyl (e.g., methyl).

1.12 Any of the preceding Formulae, wherein $R_6$ is H.

1.13 Formula I or any of Formulae 1.1-1.11, wherein $R_6$ is $C_{1-4}$alkyl (e.g., methyl).

1.14 Any of the preceding Formulae, wherein the compound is selected from a group consisting of:

8-(azetidin-1-yl)-3-methyl-1-(1-methyl-5-(p-tolyl)-1H-pyrazol-4-yl)imidazo[1,5-a]pyrazine, 8-(azetidin-1-yl)-3-methyl-1-(1-methyl-5-(4-(trifluoromethyl)phenyl)-1H-pyrazol-4-yl)imidazo[1,5-a]pyrazine, 8-(azetidin-1-yl)-3,5-dimethyl-1-(1-methyl-5-(4-(trifluoromethyl)phenyl)-1H-pyrazol-4-yl)imidazo[1,5-a]pyrazine, 8-(azetidin-1-yl)-1-(5-(4-isopropylphenyl)-1-methyl-1H-pyrazol-4-yl)-3-methyl-imidazo[1,5-a]pyrazine, 8-(azetidin-1-yl)-1-(5-(4-ethylphenyl)-1-methyl-1H-pyrazol-4-yl)-3-methylimidazo[1,5-a]pyrazine, 8-(azetidin-1-yl)-1-(5-(4-cyclopropylphenyl)-1-methyl-1H-pyrazol-4-yl)-3-methyl-imidazo[1,5-a]pyrazine;

in free or salt form.

1.15 Any of the preceding formulae wherein the compounds inhibit phosphodiesterase-mediated (e.g., PDE2-mediated) hydrolysis of cGMP, e.g., with an $IC_{50}$ of less than 1 μM, e.g., less than or equal to 250 nM, e.g., less than or equal to 50 nM.

1.16 Any of the preceding formulae wherein the compounds inhibit phosphodiesterase-mediated (e.g., PDE2-mediated), improved biophysical and physiochemical, antidepressant, and/or anxiolytic activities.

In a second aspect, the disclosure provides a pharmaceutical composition comprising a Compound of the Disclosure, i.e., Compounds of Formula I, or any of Formulae 1.1-1.16, in free or pharmaceutically acceptable salt form, in combination or association with a pharmaceutically acceptable diluents or carrier.

The disclosure also provides methods of using the Compounds of the Disclosure for treatment of PDE2-mediated disorders, e.g., disorders as set forth below (especially treatment of anxiety, depression, autism spectrum disorder (ASD), schizophrenia, cognitive impairment). This list is not intended to be exhaustive and may include other diseases and disorders as set forth below.

Therefore, in a third aspect, the disclosure provides a method for the treatment of a PDE2-mediated disorder, comprising administering to a subject in need thereof a therapeutically effective amount of a Compound of the Disclosure disclosed herein, i.e., Compounds of Formula I, or any of Formulae 1.1-1.16, in free or pharmaceutically acceptable salt form, or a pharmaceutical composition disclosed herein.

In a further embodiment of the third aspect, the disclosure provides a method for the treatment of the following disorders:

neurological disorders (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); spinal muscular atrophy; lateral sclerosis; multiple sclerosis;

cognitive disorders (including amnesia, senile dementia, HIV associated dementia, Alzheimer's associated dementia, Huntington's associated dementia, Lewy body dementia, vascular dementia, drug related dementia, delirium, and mild cognitive impairment); cognitive dysfunction associated with Parkinson's disease and depression;

mental deficiency (including Down syndrome and fragile X syndrome);

sleep disorders (including hypersomnia, circadian rhythm sleep disorder, insomnia, parasomnia, and sleep deprivation);

psychiatric disorders (such as anxiety (including acute stress disorder, generalized anxiety disorder, social anxiety disorder, panic disorder, post-traumatic stress disorder (PTSD), obsessive-compulsive disorder, specific phobia, social phobia, chronic anxiety disorder and obsessive compulsive disorder); factitious disorder (including acute hallucinatory mania);

impulse control disorders (including pathological gambling, pathological fire-setting, pathological stealing and intermittent explosive disorder);

mood disorders (including bipolar I disorder, bipolar II disorder, mania, mixed affective state, major depression, chronic depression, seasonal depression, psychotic depression and postpartum depression);

psychomotor disorders (extrapyramidal and movement disorders, e.g., Parkinsonism, Lewy body disease, tremor, drug-induced tremor, drug-induced tardive dyskinesia, L-dopa-induced dyskinesia and restless leg syndrome);

psychotic disorders (including schizophrenia (e.g., continuous or episodic, paranoid, hebephrenic, catatonic, undifferentiated and residual schizophrenic disorders), schizoaffective disorder, schizophreniform, and delusional disorder);

drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia);

pediatric psychiatric disorders (including attention deficit disorder, attention deficit/hyperactivity disorder, conduct disorder (e.g., tic disorders such as transient, chronic, motor or vocal tic disorders), autism and autism spectrum disorder (ASD));

mental and behavioral disorders due to psychoactive substance use;

cardiovascular disorder (e.g., pulmonary hypertension and pulmonary arterial hypertension);

and pain (e.g., bone and joint pain (osteoarthritis), repetitive motion pain, dental pain, cancer pain, myofascial pain (muscular injury, fibromyalgia), perioperative pain (general surgery, gynecological), chronic pain and neuropathic pain), in a subject, preferably a mammal, preferably a human, comprising administering to said subject a therapeutically effective amount of a Compound of the Disclosure disclosed herein, i.e., Compounds of Formula I, or any of Formulae 1.1-1.16, in free or pharmaceutically acceptable salt form, or a pharmaceutical composition disclosed herein.

In one embodiment, the disease or disorder is selected from a group consisting of anxiety, depression, autism spectrum disorder and schizophrenia, for example anxiety and/or depression in autistic and/or schizophrenic patients. In another embodiment, the disease or disorder is cognitive impairment associated with schizophrenia or dementia.

In the fourth aspect, the disclosure provides a Compound of the Disclosure disclosed herein, i.e., Compounds of Formula I, or any of Formulae 1.1-1.16, in free or pharmaceutically acceptable salt form (for use in the manufacture of a medicament) for the treatment of a PDE2-mediated disorder as disclosed herein.

In the fifth aspect, the disclosure provides a pharmaceutical composition comprising a Compound of the Disclosure disclosed herein, i.e., Compounds of Formula I, or any of Formulae 1.1-1.16, in free or pharmaceutically acceptable salt form, in combination or association with a pharmaceutically acceptable diluents or carrier, for use in the treatment of a PDE2-mediated disorder as disclosed herein.

DETAILED DESCRIPTION OF THE DISCLOSURE

If not otherwise specified or clear from context, the following terms herein have the following meanings:
  (a) "Alkyl" as used herein is a saturated or unsaturated hydrocarbon moiety, preferably saturated, preferably having one to six carbon atoms, preferably having one to four carbon atoms, which may be linear or branched, and may be optionally mono-, di- or tri-substituted, e.g., with halogen (e.g., chloro or fluoro), hydroxy, or carboxy.
  (b) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl) or hydroxy.
  (c) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl or hydroxy.

Compounds of the Disclosure, e.g., Compounds of Formula I, or any of Formulae 1.1-1.16, may exist in free or salt form, e.g., as acid addition salts. In this specification unless otherwise indicated, language such as "Compounds of the Disclosure" is to be understood as embracing the compounds in any form, for example free or acid addition salt form, or where the compounds contain acidic substituents, in base addition salt form. The Compounds of the Disclosure are intended for use as pharmaceuticals, therefore pharmaceutically acceptable salts are preferred. Salts which are unsuitable for pharmaceutical uses may be useful, for example, for the isolation or purification of free Compounds of the Disclosure or their pharmaceutically acceptable salts, are therefore also included. Compounds of the Disclosure may in some cases also exist in prodrug form. A prodrug form is compound which converts in the body to a Compound of the Disclosure. For example, when the Compounds of the Disclosure contain hydroxy or carboxy substituents, these substituents may form physiologically hydrolysable and acceptable esters. As used herein, "physiologically hydrolysable and acceptable ester" means esters of Compounds of the Disclosure which are hydrolysable under physiological conditions to yield acids (in the case of Compounds of the Disclosure which have hydroxy substituents) or alcohols (in the case of Compounds of the Disclosure which have carboxy substituents) which are themselves physiologically tolerable at doses to be administered. Therefore, wherein the Compound of the Disclosure contains a hydroxy group, for example, Compound-OH, the acyl ester prodrug of such compound, i.e., Compound-O—C(O)—$C_{1-4}$ alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Disclosure contains a carboxylic acid, for example, Compound-C(O)OH, the acid ester prodrug of such compound, Compound-C(O)O—$C_{1-4}$ alkyl can hydrolyze to form Compound-C(O)OH and HO—$C_{1-4}$alkyl. As will be appreciated, the term thus embraces conventional pharmaceutical prodrug forms.

The Compounds of the Disclosure herein include their enantiomers, diastereoisomers and racemates, as well as their polymorphs, hydrates, solvates and complexes. Some individual compounds within the scope of this disclosure may contain double bonds. Representations of double bonds in this disclosure are meant to include both the E and the Z isomer of the double bond. In addition, some compounds within the scope of this disclosure may contain one or more asymmetric centers. This disclosure includes the use of any of the optically pure stereoisomers as well as any combination of stereoisomers.

It is also intended that the Compounds of the Disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Disclosure may be replaced with deuterium (a stable isotope which is non-radioactive). Examples of known stable isotopes include, but not limited to, deuterium, $^{13}C$, $^{15}N$, $^{18}O$, Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the disclosure is the $^{11}C$ isotope. These radio isotopes are useful for radio-imaging and/or pharmacokinetic studies of the compounds of the disclosure. Isotopically-labeled compounds of Formula I may generally be prepared by carrying out by substituting an isotopically-labeled reagent for a non-isotopically-labeled reagent.

The phrase "Compounds of the Disclosure" or "PDE 2 inhibitors of the Disclosure" encompasses any and all of the compounds disclosed herewith, e.g., a Compounds of Formula I, or any of Formulae 1.1-1.16, as hereinbefore described, in free or salt form.

The words "treatment" and "treating" are to be understood accordingly as embracing treatment or amelioration of symptoms of the disease as well as treatment of the cause of the disease. In one embodiment, the disclosure provides a method for the treatment of the disease or disorder disclosed herein. In another embodiment, the disclosure provides a method for the prophylaxis of a disease or disorder as disclosed herein.

For methods of treatment, the word "effective amount" is intended to encompass a therapeutically effective amount to treat a specific disease or disorder.

The term "pulmonary hypertension" is intended to encompass pulmonary arterial hypertension.

The term "subject" includes human or non-human (i.e., animal). In particular embodiment, the disclosure encompasses both human and nonhuman. In another embodiment, the disclosure encompasses nonhuman. In other embodiment, the term encompasses human.

The term "comprising" as used in this disclosure is intended to be open-ended and does not exclude additional, unrecited elements or method steps.

The term "cognitive disorders" refers to any disorder comprising a symptom of cognitive deficiency (i.e., subnormal or suboptimal functioning in one or more cognitive aspects such as memory, intellect, learning, logic, attention or executive function (working memory) in an individual compared to other individuals within the same general age population). Therefore, cognitive disorders include but are not limited to amnesia, senile dementia, HIV associated dementia, Alzheimer's associated dementia, Huntington's associated dementia, Lewy body dementia, vascular dementia, drug related dementia, delirium, and mild cognitive impairment. Cognitive disorders can also be a disorder primarily but not exclusively related to psychosis (schizophrenia), mood disorders, bipolar disorders, stroke, fronto-temporal dementia, progressive supranuclear palsy, cerebral trauma and drug abuse, Asperger's syndrome and age-associated memory impairment.

Compounds of the Disclosure, e.g., Compounds of Formula I, or any of Formulae 1.1-1.16, as hereinbefore described, in free or pharmaceutically acceptable salt form may be used as a sole therapeutic agent, but may also be used in combination or for co-administration with other active agents.

Dosages employed in practicing the present disclosure will of course vary depending, e.g. on the particular disease or condition to be treated, the particular Compound of the Disclosure used, the mode of administration, and the therapy desired. Compounds of the Disclosure may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Disclosure, together with a pharmaceutically acceptable diluent or carrier therefor.

Pharmaceutical compositions comprising Compounds of the Disclosure may be prepared using conventional diluents or excipients and techniques known in the galenic art. The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus, for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof. The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream or for rectal administration as a suppository.

The compounds of the Disclosure herein and their pharmaceutically acceptable salts may be made using the methods as described and exemplified herein and by methods similar thereto and by methods known in the chemical art. Such methods include, but are not limited to, those described below. If not commercially available, starting materials for these processes may be made by procedures, which are selected from the chemical art using techniques which are similar or analogous to the synthesis of known compounds. All references cited herein are hereby incorporated by reference in their entirety.

EXAMPLES

Example 1: Synthesis of 8-(azetidin-1-yl)-3-methyl-1-(1-methyl-1H-pyrazol-4-yl)imidazo[1,5-a]pyrazine The title compound is synthesized according to scheme 1 shown below.

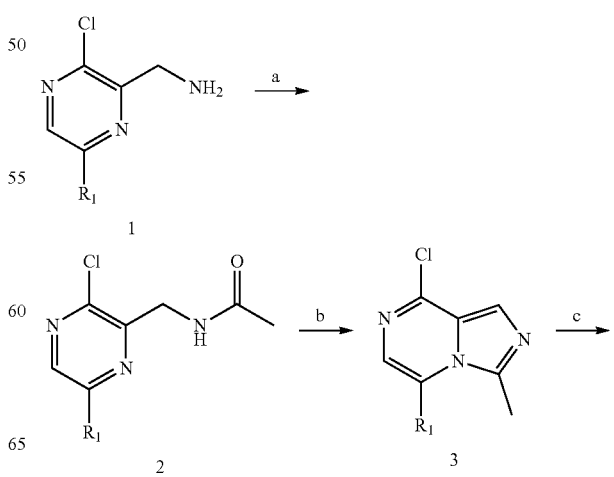

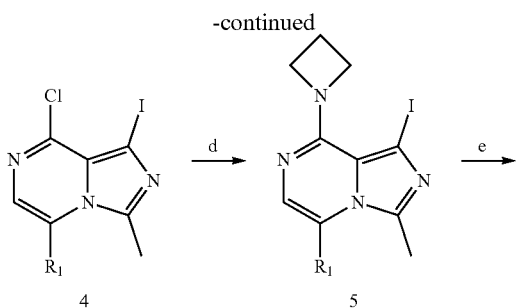

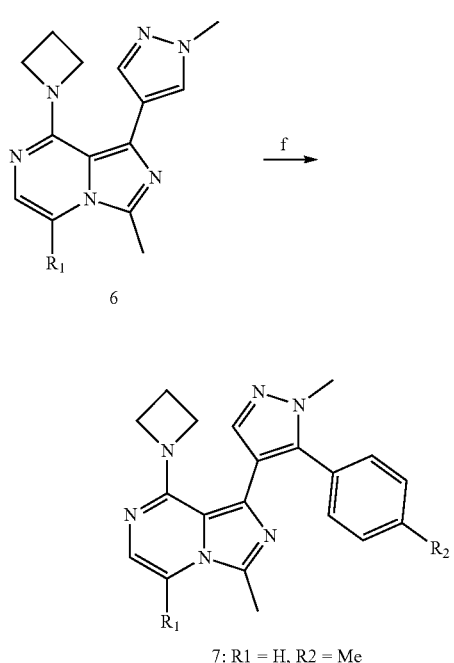

7: R1 = H, R2 = Me

(2): N-((3-chloropyrazin-2-yl)methyl)acetamide (R1=H)

To a stirred suspension of (3-chloropyrazin-2-yl)methanamine hydrochloride (500 mg, 2.78 mmol) in ethyl acetate (10 mL) was added acetic anhydride (315 µL, 3.33 mmol) dropwise, followed by triethylamine (1.16 mL, 8.34 mmol). The mixture was stirred at room temperature for 1 h, and the solvent was removed under reduced pressure. The obtained residue was dissolved in methylene chloride (150 mL) and washed with saturated NaHCO3 (2×25 mL). The organic phase was evaporated under reduced pressure and was further dried under high vacuum to give the title compound as a beige solid (376 mg, 72.9% yield), which was directly used for the next reaction without further purification. MS (ESI) m/z 186.0507 [M+H]+. 1H NMR (500 MHz, Chloroform-d) δ 8.5 (d, J=2.51 Hz, 1H), 8.3 (d, J=2.55 Hz, 1H), 4.7-4.7 (m, 2H), 2.1 (s, 3H)).

(3): 8-chloro-3-methylimidazo[1,5-a]pyrazine (R$_1$=H)

To a stirred suspension of N-[(3-chloropyrazin-2-yl)methyl]acetamide (340 mg, 1.83 mmol) in acetonitrile (4 mL) was added POCl$_3$ (850 µL, 9.14 mmol) dropwise, followed by two drops of DMF. The mixture was stirred at 60° C. for 1.5 h, and the solvent was removed under reduced pressure. The obtained residue was dissolved in ethyl acetate (100 mL) and washed with saturated Na$_2$CO$_3$ (2×25 mL) and brine (25 mL) successively. The organic phase was evaporated under reduced pressure and was further dried under high vacuum to afford the title compound as a beige solid (329 mg, 107% yield, the crude product may contain salt), which was directly used for the next reaction without further purification. MS (ESI) m/z 168.0475 [M+H]+.

(4): 8-chloro-1-iodo-3-methylimidazo[1,5-a]pyrazine (R$_1$=H)

A solution of 8-chloro-3-methylimidazo[1,5-a]pyrazine (270 mg, 1.61 mmol) and N-iodosuccinimide (506 mg, 2.25 mmol) in anhydrous DMF (1.5 mL) was degassed twice with argon, and then stirred at 110° C. for 24 h. Another batch of iodosuccinimide (506 mg, 2.25 mmol) was added. The reaction mixture was continued to stir at 70° C. for 12 h, and the solvent was removed under reduced pressure. The obtained crude product was purified by silica-gel column chromatography using a gradient of 0-100% ethyl acetate in hexane as eluent to afford the title compound as a light orange solid (414 mg, 88% yield). MS (ESI) m/z 293.9383 [M+H]+. 1H NMR (500 MHz, Chloroform-d) δ 7.6-7.5 (m, 1H), 7.4-7.3 (m, 1H), 2.8 (s, 3H).

(5): 8-(azetidin-1-yl)-1-iodo-3-methylimidazo[1,5-a]pyrazine (R$_1$=H)

A mixture of 8-chloro-1-iodo-3-methylimidazo[1,5-a]pyrazine (209 mg, 0.71 mmol), azetidine hydrochloride (140 mg, 1.49 mmol), and triethylamine (400 µL, 2.87 mmol) in anhydrous DMF (2 mL) was stirred at room temperature overnight. The solvent was removed under reduced pressure and the residue was dissolved in ethyl acetate (150 mL). The resulting solution was washed with 1 N NaOH (3×40 mL), and the organic phase was evaporated to dryness, the obtained residue was further dried under high vacuum to afford the title compound as a pale solid (137 mg, 61% yield), which was directly used for the next reaction without further purification. MS (ESI) m/z 315.0381 [M+H]+.

(6): 8-(azetidin-1-yl)-3-methyl-1-(1-methyl-1H-pyrazol-4-yl)imidazo[1,5-a]pyrazine (R$_1$=H)

A mixture of 8-(azetidin-1-yl)-1-iodo-3-methylimidazo[1,5-a]pyrazine (500 mg, 1.59 mmol), (1-methyl-1H-pyrazol-4-yl)boronic acid (401 mg, 3.183 mmol), potassium carbonate (659 mg, 4.78 mmol), and tetrakis(triphenylphosphine)palladium(0) (185 mg, 0.16 mmol) in a mixture of NMP (1 mL), EtOH (4 mL) and water (0.15 mL) was degassed twice with argon, and then heated at 100° C. by microwave for 3 h. The solvents were removed under reduced pressure, and the residue was dissolved in ethyl acetate (50 mL). The resulting solution was washed with 1 N NaOH (2×4 mL), and evaporated to dryness. The residue was purified by silica-gel column chromatography using a gradient of 0-100% ethyl acetate in hexane as eluent to yield the title product as a chocolate oil (200 mg, yield 47%). MS (ESI) m/z 269.1748 [M+H]+. 1H NMR (500 MHz, Chloroform-d) δ 7.7 (s, 1H), 7.7 (s, 1H), 7.1 (d, J=5.11 Hz, 1H), 7.1 (d, J=5.10 Hz, 1H), 4.0 (s, 4H), 2.6 (s, 3H), 2.3-2.2 (m, 2H).

(7): 8-(azetidin-1-yl)-3-methyl-1-(1-methyl-5-(p-tolyl)-1H-pyrazol-4-yl)imidazo[1,5-a]pyrazine (R₁=H, R₂=Me)

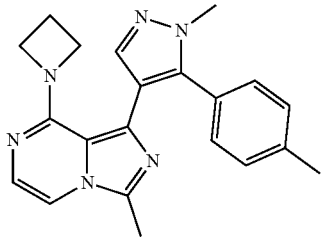 [SMILES: Cc1ccc(-c2c(-c3nc(C)n4ccnc(N5CCC5)c34)cnn2C)cc1]

A suspension of 8-(azetidin-1-yl)-3-methyl-1-(1-methyl-1H-pyrazol-4-yl)imidazo[1,5-a]pyrazine (58 mg, 0.224 mmol), 1-bromo-4-methylbenzene (33 μL, 0.268 mmol), pivalic acid (11 mg, 0.112 mmol) and potassium carbonate (93 mg, 0.672 mmol) in toluene (1 mL) was degassed with argon, and di(adamantan-1-yl)(butyl)phosphine (19 mg, 0.054 mmol) and palladium acetate (13 mg, 0.045 mmol) were added. The mixture was degassed with argon again and then heated at 125° C. for 24 h. After the solvent was removed under reduced pressure, the residue was purified with a semipreparative HPLC system using a gradient of 0-18% acetonitrile in water containing 0.1% formic acid over 16 min to afford the title compound as an off-white solid (28 mg, 35% yield). MS (ESI) m/z 359.2108 [M+H]⁺. ¹H NMR (500 MHz, Chloroform-d) δ 7.67 (s, 1H), 7.31 (d, J=7.8 Hz, 1H), 7.22-7.19 (m, 2H), 7.15 (d, J=8.1 Hz, 2H), 7.08-6.99 (m, 2H), 4.60 (d, J=8.2 Hz, 1H), 3.93 (s, 1H), 3.90 (s, 3H), 3.70 (d, J=7.2 Hz, 1H), 3.61 (d, J=7.3 Hz, 1H), 2.64 (s, 2H), 2.60 (s, 1H), 2.46 (s, 1H), 2.38 (s, 2H), 2.37-2.30 (m, 2H).

Examples 2 to 6 were prepared in an analogous fashion following the procedure described in the synthesis step 7 of the Example 1.

Example 2: 8-(azetidin-1-yl)-1-(5-(4-ethylphenyl)-1-methyl-1H-pyrazol-4-yl)-3-methylimidazo[1,5-a]pyrazine (8, R₁=H, R₂=Et)

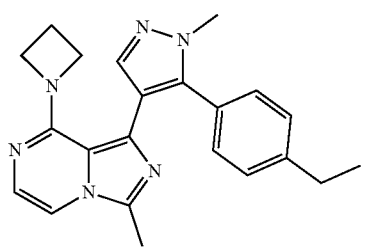 [SMILES: CCc1ccc(-c2c(-c3nc(C)n4ccnc(N5CCC5)c34)cnn2C)cc1]

MS (ESI) m/z 373.2778 [M+H]⁺. ¹H NMR (500 MHz, Chloroform-d) δ 7.6 (s, 1H), 7.3 (d, J=8.17 Hz, 2H), 7.2-7.2 (m, 2H), 7.1 (d, J=5.07 Hz, 1H), 7.0 (d, J=5.05 Hz, 1H), 3.9 (s, 3H), 3.9-3.8 (m, 4H), 2.7-2.6 (m, 2H), 2.6 (s, 3H), 2.2-2.1 (m, 2H), 1.2 (t, J=7.61 Hz, 3H).

Example 3: 8-(azetidin-1-yl)-1-(5-(4-isopropylphenyl)-1-methyl-1H-pyrazol-4-yl)-3-methyl-imidazo[1,5-a]pyrazine (9, R₁=H, R₂=ⁱPr)

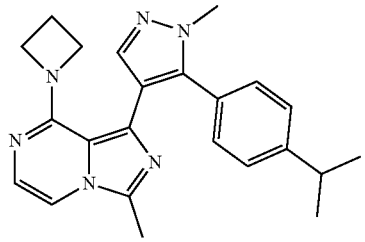 [SMILES: Cc1nc(-c2cnn(C)c2-c2ccc(C(C)C)cc2)c2c(N3CCC3)nccn12]

MS (ESI) m/z 387.3552 [M+H]⁺. ¹H NMR (500 MHz, Chloroform-d) δ 7.6 (s, 1H), 7.3 (d, J=8.17 Hz, 2H), 7.2 (d, J=8.14 Hz, 2H), 7.1 (d, J=5.02 Hz, 1H), 7.0 (d, J=5.01 Hz, 1H), 3.9 (s, 3H), 3.8 (s, 4H), 2.9-2.8 (m, 1H), 2.6 (s, 3H), 2.3-2.1 (m, 2H), 1.2-1.2 (m, 6H).

Example 4: 8-(azetidin-1-yl)-1-(5-(4-cyclopropylphenyl)-1-methyl-1H-pyrazol-4-yl)-3-methyl-imidazo[1,5-a]pyrazine (10, R₁=H, R₂=cyclopropyl)

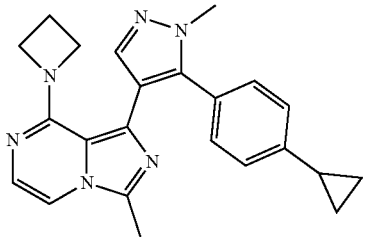 [SMILES: Cc1nc(-c2cnn(C)c2-c2ccc(C3CC3)cc2)c2c(N3CCC3)nccn12]

MS (ESI) m/z 385.2129 [M+H]⁺. ¹H NMR (500 MHz, Chloroform-d) δ 7.9 (s, 1H), 7.2 (d, J=8.23 Hz, 2H), 7.1 (d, J=8.35 Hz, 2H), 6.2 (s, 1H), 5.6 (s, 1H), 4.7-4.6 (m, 1H), 3.9 (s, 3H), 3.8-3.7 (m, 1H), 3.7-3.5 (m, 2H), 2.7 (s, 3H), 2.0-2.0 (m, 2H), 1.3-1.2 (m, 1H), 1.1-1.0 (m, 2H), 0.9-0.8 (m, 2H).

Example 5: 8-(azetidin-1-yl)-3-methyl-1-(1-methyl-5-(4-(trifluoromethyl)phenyl)-1H-pyrazol-4-yl)imidazo[1,5-a]pyrazine (11, R₁=H, R₂=trifluoromethyl)

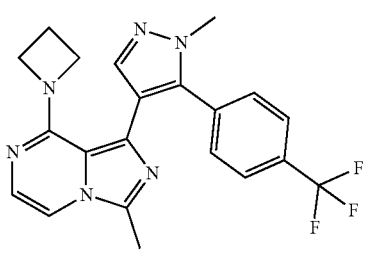 [SMILES: Cc1nc(-c2cnn(C)c2-c2ccc(C(F)(F)F)cc2)c2c(N3CCC3)nccn12]

MS (ESI) m/z 413.1313 [M+H]⁺. ¹H NMR (500 MHz, Chloroform-d) δ 7.7 (d, J=2.12 Hz, 2H), 7.6 (s, 1H), 7.6-7.5 (m, 2H), 7.1 (d, J=5.30 Hz, 1H), 7.0 (d, J=5.32 Hz, 1H), 4.0 (s, 4H), 3.9 (s, 3H), 2.6 (s, 3H), 2.3 (t, J=7.80 Hz, 2H).

Example 6: 8-(azetidin-1-yl)-3,5-dimethyl-1-(1-methyl-5-(4-(trifluoromethyl)phenyl)-1H-pyrazol-4-yl)imidazo[1,5-a]pyrazine (12, $R_1$=Me, $R_2$=trifluoromethyl)

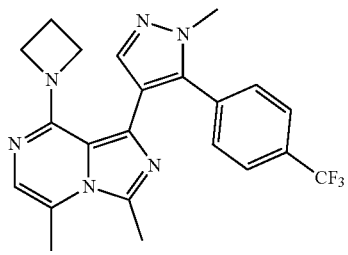 [SMILES: Cc1cnc(N2CCC2)c2c(-c3cnn(C)c3-c3ccc(C(F)(F)F)cc3)nc(C)n12]

MS (ESI) m/z 427.2861 [M+H]$^+$. $^1$H NMR (500 MHz, Chloroform-d) δ 7.8 (dd, J=7.91, 14.49 Hz, 2H), 7.7 (d, J=7.41 Hz, 1H), 7.7 (d, J=7.96 Hz, 1H), 7.6 (d, J=8.02 Hz, 1H), 7.0 (s, 1H), 4.9 (d, J=97.14 Hz, 2H), 3.9 (s, 3H), 3.6 (d, J=49.04 Hz, 2H), 2.5 (d, J=16.41 Hz, 3H), 2.4 (s, 3H), 2.0 (d, J=37.87 Hz, 2H).

Example 7: Measurement of PDE2 Inhibition In Vitro r-hPDE2A (Accession No. NM_002599, *Homo sapiens* phosphodiesterase 2A, cGMP-stimulated, transcript variant 1) A mammalian expression cloning vector with recombinant cDNA copy of the gene is purchased from Origene. Protein is expressed via transient transfection of HEK293 cells. The cells are harvested at 48 hours after transfection, washed once with TBS buffer (50 mM Tris-HCl, pH 7.5, 150 mM NaCl), then lysed by sonication in cold homogenization buffer (50 mM Tris-HCl, pH 7.5, 5 mM $MgCl_2$, 1× protease inhibitor cocktail). The homogenate is centrifuged for 30 min at 15,000 g at 4° C. to obtain the soluble cytosolic fraction. The protein concentration of the cytosol is determined using BCA Protein Assay Kit (Pierce) with bovine serum albumin as a standard.

Assay: PDE2A is assayed with FL-cAMP as substrate. An enzyme titration is first performed to determine the working concentration of PDE. The concentration of the enzyme giving activity of 100 AmP in the absence of inhibitor is deemed an appropriate working concentration for PDE.

PDE enzyme is diluted in a standard reaction buffer (10 mM Tris-HCl pH 7.2, 10 mM $MgCl_2$, 0.1% BSA, 0.05% $NaN_3$) according to the titration curve. For PDE2 assay the reaction buffer is supplemented with 1 μM cGMP to fully activate the enzyme. 99 μl of diluted enzyme solution is added into each well in a flat bottom 96-well polystyrene plate and then ~1 μl of test compound dissolved in 100% DMSO is added. The compounds are mixed and pre-incubated with the enzyme for 10 min at room temperature.

The FL-cNMP conversion reaction is initiated by addition of substrate (45 nM final). Enzyme and inhibitor mix (16 μl) and substrate solution (4 μl of 0.225 μM) are combined in a 384-well microtiter plate. The reaction is incubated in the dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Amp).

A decrease in cAMP concentration, measured as decreased Amp, is indicative of inhibition of PDE activity. $IC_{50}$ values are determined by measuring enzyme activity in the presence of 8 to 16 concentrations of compound ranging from 0.00037 nM to 80,000 nM and then plotting drug concentration versus ΔmP. Test well values are normalized to control reactions run on the same plate (values converted to % of control). $IC_{50}$ values are estimated using nonlinear regression software, fitting a four-parameter one-site dose-response model (XLFit; IDBS, Cambridge, Mass.). Bottom of curve is fixed at 0% of control.

Quality Controls: To determine the IC50 of an inhibitor, an enzyme concentration that gave optimal signal range of 100-200 milli-polarization units is selected. The total fluorescence intensity of each sample well is measured to calculate the average and standard deviation. If the total fluorescence intensity of any sample well is not within the range of Average ±3SD, the mp value of that particular well is discarded.

Using the IMAP procedure described or similarly described above, we screened a proprietary PDE-focused compound library to identify novel compounds with nanomolar PDE2 inhibitory activities. An exemplified compound of the Disclosure (e.g. the compound of Examples 1) are tested and shown be active at nanomolar concentrations, e.g., as follows: The $IC_{50}$ calculated for the compound of Example 1 above (i.e., formula 1) are shown in the Table 1 below. A ratio for each isoform with PDE2 is used to determine specificity.

TABLE 1

PDE Inhibition Constant of Compound 1

| $IC_{50}$ (μM) | PDE1 | PDE2 | PDE3 | PDE4 | PDE5 | PDE6 | PDE7B | PDE8A | PDE9A | PDE10A | PDE11A |
|---|---|---|---|---|---|---|---|---|---|---|---|
| Compound 1 | 8.3 | 0.035 | >100 | 24.8 | 15.1 | >100 | 19.7 | >100 | >100 | 4.3 | >100 |

TABLE 2

Selectivity of Compound 1 Relative to PDE2

| $IC_{50}$ (μM) | PDE1 | PDE2 | PDE3 | PDE4 | PDE5 | PDE6 | PDE7B | PDE8A | PDE9A | PDE10A | PDE11A |
|---|---|---|---|---|---|---|---|---|---|---|---|
| PDEX/PDE2 | 240 | 1 | >2870 | 713 | 434 | >2870 | 566 | >2870 | >2870 | 124 | >2870 |

Commercially available inhibitory Bay 7550 is used as a comparative positive control. BAY-7550 was run through similar assays, and it was found that Compound 1 shows far greater selectivity for PDE2 than BAY-7550, a known PDE2 inhibitor.

Example 8: Pharmacokinetic Study in Mice

Mice are given a single oral dose of the compound to be tested (10 mg/kg, PO) and plasma and brain availability are measured (0.25-4h) using HPLC and LC-MS using methods analogous to those described in Zhao et al., *J. Chromatogr. B. Analyt. Technol. Biomed. Life Sci.* (2005) 819(1):73-80 and Appels, N. M., et al., *Rapid Commun. Mass Spec.* 2005. 19(15): p. 2187-92. As shown in the Table 3 below, Compound 1 showed a potent $IC_{50}$ of 34 nM and significantly better blood brain barrier cross-over and brain penetration in comparison with BAY-7550.

TABLE 3

Mouse Pharmacokinetic Data

| Compound | PDE2A $IC_{50}$ (µM) | T1/2 (hr) | Tmax | Cmax | AUC (0-4 hr area, ng-hr/mL) | B/P |
|---|---|---|---|---|---|---|
| Cmpd 1 | 0.0347 | 0.8 | 0.5 | 268 | 119 | 0.3 |
| BAY-7550 | 0.0008 | ND | 0.25 | 3 | ND | 0.04 |

Example 9: Evaluation of the Effect of Novel PDE2A Inhibitor, of Formula 1, on cGMP Signaling in Hippocampal Cells and in Brain Compound 1 (i.e., the compound synthesized in Example 1 above) was tested for its ability to increase cGMP and cAMP levels in HT-22 (hippocampal-like) cells. The compound showed a dose-dependent increase in cGMP levels stimulated by NMDA (20 µM) during a 15 min incubation period with maximum effect seen at 0.011M concentration. Similarly, a dose-dependent increase in cAMP levels in HT22 cells stimulated by noradrenergic agonist (cAMP activator) isoproterenol (ISO, 10 nM) was observed with a maximum level reaching with 0.01 µM of Compound 1. At a concentration of 0.01 µM, Compound 1 induced long-lasting elevations in cGMP and cAMP levels in HT22 cells that was observable for even after 24h. The optimal dose for stimulation of both cGMP and cAMP levels in these assays was 10 nM, which is comparable to the calculated PDE2A $IC_{50}$ value for the formula 1 compounds in an in vitro assay (PDE2A $IC_{50}$ is 35 nM), indicating a good agreement between affinity of Compound 1 for the target of interest and the resulting modulation of cNT levels.

Compound 1 was also tested for its ability to elevate the phosphorylation state of effector proteins under the control of cGMP and/or cAMP signaling pathways. The compound induced a concentration-dependent increase in the phosphorylation of three substrates known to be regulated by cyclic nucleotide signaling cascades, namely, phosphorylation of VASP (vasodilator stimulated phosphoprotein) and CREB (cAMP response element-binding protein) and increased the expression of the growth factor BDNF. The peak increases in phospho-VASP, phospho-CREB, and BDNF expression were observed at the approximately the same drug concentration (0.01 µM) corresponding to that observed to yield maximal elevation of cNT levels in cells and selective inhibition of PDE2A in vitro.

Example 10: Evaluation of the Effects of Novel PDE2A Inhibitors on Depression- and Anxiety-Like Behaviors Compound 1 was evaluated for acute antidepressant-like activity using the forced swim and tail suspension paradigms in mice. The PDE2A inhibitor, BAY-7550 and the antidepressant medication, desipramine were used as comparators for these tests. Desipramine induced signs of antidepressant-like activity, and BAY-7550 showed generally smaller effects that did not reach significance in all assays. Compound 1, on the other hand, significantly reduced immobility time (i.e., had antidepressant-like activity) in both tests.

The compound of formula 1 (1, 2, and 5 mg/kg, i.p.) was evaluated for acute anxiolytic activity using the elevated plus maze and hole board paradigms in mice. Diazepam (0.5 mg/kg, i.p.) induced signs of anxiolytic activity in both paradigms (e.g., increased entrance into open arms in elevated plus maze; increased explorations in the hold board test). The commercial PDE2 inhibitor showed no statically significant effect in these experiments, but unexpectedly, the compound of formula 1 significantly increased open arm entrances (elevated plus maze) and increased exploration in the hole-board test in a dose-dependent manner. Importantly, the same dose levels of the compound and diazepam that increased anxiolytic activity did not significantly affect spontaneous locomotor activity in mice which, suggests that these effects were not due to non-selective psychomotor actions.

Compound 1 was also evaluated for acute anxiolytic activity using the elevated plus maze and hole board paradigms in mice. The PDE2A inhibitor BAY-7550 and the anxiolytic medication diazepam were used as comparators for these tests. Diazepam induced signs of anxiolytic activity in both paradigms (e.g., increased entrance into open arms in elevated plus maze and increased explorations in the hold board test). BAY-7550 resulted in small trends for these assays that did not achieve statistical significance. Compound 1, however, significantly increased open arm entrances (elevated plus maze) and increased exploration in the holeboard test in a dose-dependent manner. Importantly, the same dose levels of Compound 1 and diazepam that increased anxiolytic activity did not significantly affect spontaneous locomotor activity in mice, suggesting that these effects were not due to non-selective psychomotor actions.

Finally, dose levels of Compound 1, in addition to the comparator compounds effective in paradigms for detection of antianxiety-like activity were tested for effects on in vivo levels of cGMP and cAMP in the mouse brain. For these studies, mice were killed 30 min after injection of each drug/dose and hippocampus isolated and used for measurement of cyclic nucleotides. The compound induced significant increases in both cGMP and cAMP levels in hippocampus.

What is claimed is:

1. A Compound of Formula I

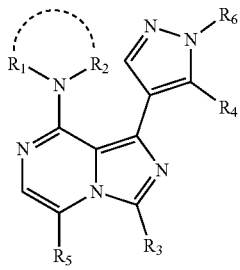

Formula I wherein
(i) $R_1$ and $R_2$ together with the nitrogen atom form an unsubstituted heteroC$_{3-7}$cycloalkyl;
(ii) $R_3$ is H or C$_{1-4}$alkyl;
(iii) $R_4$ is heteroaryl, halo, cyano or aryl optionally substituted with one or more groups selected from C$_{1-4}$alkyl, C$_{3-7}$cycloalkyl, C$_{1-4}$alkoxy and haloC$_{1-4}$alkyl;
(iv) $R_5$ is H or C$_{1-4}$alkyl;
(v) $R_6$ is H or C$_{1-4}$alkyl;
in free or salt form.

2. The compound according to claim 1, wherein $R_1$ and $R_2$ together with the nitrogen atom form an azetidin-1-yl.

3. The compound according to claim 1, wherein $R_3$ is C$_{1-4}$alkyl.

4. The compound according to claim 1, wherein $R_4$ is aryl substituted with one or more groups selected from C$_{1-4}$alkyl, C$_{3-7}$cycloalkyl, C$_{1-4}$alkoxy and haloC$_{1-4}$alkyl.

5. The compound according to claim 1, wherein $R_4$ is aryl substituted with C$_{1-4}$alkyl.

6. The compound according to claim 1, wherein $R_4$ is aryl substituted with C$_{3-7}$cycloalkyl.

7. The compound according to claim 1, wherein $R_4$ is aryl substituted with C$_{1-4}$alkoxy.

8. The compound according to claim 1, wherein $R_4$ is aryl substituted with haloC$_{1-4}$alkyl.

9. The compound according to claim 1, wherein $R_5$ and $R_6$ are H.

10. The compound according to claim 1, wherein the compound is selected from the group consisting of:
8-(azetidin-1-yl)-3-methyl-1-(1-methyl-5-(p-tolyl)-1H-pyrazol-4-yl) imidazo[1,5-a]pyrazine,
8-(azetidin-1-yl)-3-methyl-1-(1-methyl-5-(4-(trifluoromethyl)phenyl)-1H-pyrazol-4-yl) imidazo[1,5-a]pyrazine,
8-(azetidin-1-yl)-3,5-dimethyl-1-(1-methyl-5-(4-(trifluoromethyl)phenyl)-1H-pyrazol-4-yl) imidazo[1,5-a]pyrazine,
8-(azetidin-1-yl)-1-(5-(4-isopropylphenyl)-1-methyl-1H-pyrazol-4-yl)-3-methyl-imidazo[1,5-a]pyrazine,
8-(azetidin-1-yl)-1-(5-(4-ethylphenyl)-1-methyl-1H-pyrazol-4-yl)-3-methylimidazo[1,5-a]pyrazine, and
8-(azetidin-1-yl)-1-(5-(4-cyclopropylphenyl)-1-methyl-1H-pyrazol-4-yl)-3-methyl-imidazo[1,5-a]pyrazine;
in free or salt form.

11. A pharmaceutical composition comprising the compound according to claim 1, in combination or association with a pharmaceutically acceptable diluent or carrier.

12. A method for the treatment of a PDE2 mediated disorder comprising administering to a subject in need thereof the pharmaceutical composition according to claim 11.

13. The method of claim 12, wherein the disorder is selected from the group consisting of neurological disorders epilepsy; Alzheimer's disease; Parkinson's disease; brain injury; stroke; cerebrovascular diseases; spinal muscular atrophy; lateral sclerosis; multiple sclerosis; cognitive disorders; cognitive dysfunction associated with Parkinson's disease and depression; mental deficiency; sleep disorders; psychiatric disorders; factitious disorder; impulse control disorders; mood disorders; psychomotor disorders; psychotic disorders; drug dependence; eating disorders; pediatric psychiatric disorders; mental and behavioral disorders due to psychoactive substance use; cardiovascular disorder; and pain.

14. The method of claim 12 wherein the disorder is selected from the following: anxiety, depression, autism spectrum disorder, schizophrenia, anxiety and/or depression in autistic and/or schizophrenic patients, and cognitive impairment associated with schizophrenia or dementia.

15. The compound according to claim 1, wherein $R_3$ is methyl.

16. The compound according to claim 1, wherein $R_6$ is methyl.

17. The compound according to claim 1, wherein $R_4$ is phenyl optionally substituted with methyl, ethyl, or isopropyl.

18. The compound according to claim 1, wherein $R_4$ is phenyl optionally substituted with cyclopropyl.

19. The compound according to claim 1, wherein $R_4$ is phenyl optionally substituted with methoxy.

20. The compound according to claim 1, wherein $R_4$ is phenyl optionally substituted with trifluoromethyl.

* * * * *